(12) United States Patent
Dickie et al.

(10) Patent No.: US 6,337,632 B1
(45) Date of Patent: Jan. 8, 2002

(54) SUMP PUMP AND MOISTURE ALARM

(75) Inventors: Robert G. Dickie, Newmarket; Angelo Orsi, Keswick, both of (CA)

(73) Assignee: Orsi Homes Limited, Ontario (CA)

( * ) Notice: Subject to any disclaimer, the term of this patent is extended or adjusted under 35 U.S.C. 154(b) by 0 days.

(21) Appl. No.: 09/811,463

(22) Filed: Mar. 20, 2001

(51) Int. Cl.$^7$ .............................................. G08B 21/00
(52) U.S. Cl. .................... 340/620; 340/604; 340/691.1; 340/693.5; 73/304 R; 200/61.04
(58) Field of Search ................................ 340/604, 605, 340/618, 620, 691.1, 693.5; 73/304 R; 200/61.04

(56) References Cited

U.S. PATENT DOCUMENTS

| | | | |
|---|---|---|---|
| 3,874,403 A | 4/1975 | Fischer | |
| 4,020,478 A | 4/1977 | Hatfield | |
| 4,216,468 A | * 8/1980 | Kaufmann | 340/620 |
| 4,673,925 A | * 6/1987 | Whiteman | 340/620 |
| 4,796,658 A | 1/1989 | Caple | |
| 5,314,313 A | * 5/1994 | Janesky | 340/620 |
| 5,325,086 A | * 6/1994 | Thomas | 340/620 |
| 5,483,227 A | 1/1996 | Kuo et al. | |
| 5,517,174 A | 5/1996 | Barrows | |
| 5,562,423 A | 10/1996 | Orth et al. | |
| 5,927,955 A | 7/1999 | Janesky | |
| 6,069,331 A | 5/2000 | Utke | |
| 6,140,925 A | 10/2000 | Lee et al. | |
| 6,157,307 A | 12/2000 | Hardin | |

* cited by examiner

*Primary Examiner*—Daniel J. Wu
(74) *Attorney, Agent, or Firm*—Marks & Clerk (57) ABSTRACT

A self-contained apparatus which will detect the presence of moisture at floor level—such as on a basement floor—or below floor level—such as the level of water in a sump. The apparatus is battery powered and foldable, with a pair of moisture sensing electrodes located at the end of a sensor arm that is hingedly connected to a base. A mast is hingedly connected at the other end of the base, and in its erected condition, all of the operating and alarm circuits of the moisture sensing apparatus are located at a distance above the floor. When the sensor arm extends downwardly into a sump, if the moisture rises in the sump well higher than a predetermined level, an alarm will be given.

13 Claims, 6 Drawing Sheets

SUMP PUMP AND MOISTURE ALARM

FIELD OF THE INVENTION

This invention relates to apparatus for detecting the presence of moisture, and also for detecting instances where sump pump failure has occurred. Specifically, the present invention is directed to a self-contained apparatus which functions in either of two modes: as a moisture sensor for sensing excessive amount of moisture at floor level; and as a water level sensor for giving an alarm when the water level in a sump well rises beyond a predetermined level.

BACKGROUND OF THE INVENTION

Many, but not all, homes are equipped with a sump well in their basements and a pump within the well which pumps water away when the water level reaches a pre-determined level. Other homes that are not equipped with sump pumps may also be subject to flooding under certain conditions.

In homes which are equipped with sump wells and sump pumps, perimeter drainage is arranged on the inside of the basement walls below the floor, and that perimeter drainage feeds into the sump well. Thus, water which seeps below the basement walls and/or runs below the poured concrete floor of the basement will find its way into the perimeter drainage, which functions somewhat as a weeper bed in reverse in that collects moisture rather than disseminates it, and water which does seep into the perimeter drainage is then fed through the gently sloped tiles into the sump well. The sump pump is usually controlled by a float valve or float control of some sort, so that when water rises beyond a certain level in the sump well, the sump pump turns on and pumps water away from the well to a remote drain located beyond the outside walls of the building—such as into a weeper bed, a septic tank, or into a ditch.

However, sump pumps—or, at least, the controls which turn sump pumps on when the water level in the sump well reaches a predetermined level—are prone to failure. Very often, especially in flooding conditions, the water may rise too quickly and a float valve may jam. Also, in other circumstances, because the sump pump is connected to the electrical supply system for the building, in storm conditions the electrical supply may be off, and, in any event, it is possible that the sump pump, when it starts, may blow a fuse or trip a breaker which is installed for protection purposes in the fuse panel or breaker panel.

Accordingly, there are a number of products in the market and which are found in the prior art which function to provide an alarm when the sump pump has failed to operate properly. Regrettably, many of those products are connected to the same electrical supply as the sump pump, and in conditions of general power failure in the building or region, the alarm will fail to work as well.

Many buildings, particularly large custom homes that are built in rural areas, have sump pumps, and will have an emergency or portable power supply that can be started and utilized in the event of power failure. However, as noted above, if an alarm system is connected to the same power supply as the sump pump, no alarm may be given when it is needed most.

Other circumstances exist in homes that have no basement, or in homes or other buildings that have a basement but do not have a sump well and sump pump. Those homes and other buildings are also subject to flooding, either because of seepage through or under the walls, or sometimes as a consequence of overflow of a water-using appliance such as a clothes washer or dish washer. Sometimes, as well, a water pipe may freeze and break, or other catastrophes occur, whereby the floor is flooded. Usually, however, when a floor starts to flood—particularly as a consequence of seepage of water from the outside, overflow of an appliance, or imminent breakage of a water pipe—there may be just a small accumulation of water in the first instance.

Nonetheless, that small accumulation of water can, in time, amount to a considerable amount of water; and by the time that considerable amount of water is detected, damage may have occurred to walls, furniture, books, boxes, or anything else stored on or in contact with the floor.

There are also a number of products known in the market which sit against the floor and detect moisture—either extremely high relative humidity, or more likely an accumulation of water even to a depth of one or two millimetres.

However, many of those floor-mounted or floor-contacting sensors are self-contained, much the same way as a small smoke alarm is self-contained and, if the rise of water on the floor is too rapid, the moisture sensor may effectively be drowned. Other moisture sensors are capable of floating.

Once again, however, many such sensors are powered by the electrical distribution system in the building. Accordingly, if the electrical power goes out, so does the floor-mounted moisture sensor. Others are battery powered, but typically a battery powered, floor-mounted moisture sensor is one where the electronics are self-contained and it is subject to damage even as it does its job in detecting moisture.

Alarms which are particularly intended for mounting inside a sump well are typically more complicated than those which mount to the floor, so much so that they may require the services of a licensed electrician and/or a licensed plumber to be installed The present inventors have unexpectedly discovered that a simple, self-contained, foldable apparatus may be provided wherein the apparatus can operate in either of two modes—either as a floor moisture sensor, or a sensor which detects rise of water in a sump well beyond a predetermined level. In either mode, the electrical operating and alarm circuits are raised above the floor in a mast portion of the apparatus, so that they are protected from flooding or drowning. The apparatus is self-contained, so that it is battery powered.

Because the moisture sensing circuits themselves are essentially passive circuits, a battery powered self-contained moisture sensing apparatus in keeping with the present invention will have remarkably long battery life, except if it goes into alarm condition, in which case the operating and alarm circuits become active and power consuming circuits.

Of course, the present invention contemplates that, when moisture is sensed, an audible alarm will be given by such as a horn, bell, or buzzer, which is built into the apparatus. At the same time, additional circuitry can be provided whereby in an alarm condition, a signal is emitted for reception at a remote receiver—which may be as many as 15 or 30 metres away from the moisture sensor, in another part of the building. Nonetheless, an alarm signal is given when moisture is sensed, or when the water level in a sump well reaches a predetermined level. The election as to which mode the moisture sensor of the present invention will operate is, of course, made by the user, at the time that the apparatus is put into its operating configuration, and into place for operation.

A typical sump well installation is such that an apparatus or sensor will be mounted to detect when the water level in the sump well rises to within 20 or 25 centimetres of the floor level of the floor into which the sump well has been sunk. That allowance for rising water assures that, if the water reaches the predetermined level and the alarm is given and heeded, typically there will be quite sufficient time to determine if there has been a pump failure or an electrical failure, and to arrange for repair or the provision of auxiliary power or pumping equipment, if necessary. Typically, the diameter of a sump well is about 80 to 120 centimetres, so it may take some considerable time for water to rise and additional 20 to 25 centimetres before flooding occurs as a consequence of the overflow of the sump well.

Indeed, a principal operating configuration of the apparatus of the present invention is as an alarm device for use in association with sump wells, so as to provide a warning in the event that a level of water in the sump well rises above a predetermined level.

Accordingly, in a simpler embodiment of the present invention intended only for use in association with sump wells, the structure of the apparatus is somewhat more simplified because the sensor arm may be fixed in place, rather than being hingable for operation in either of the two modes discussed above.

DESCRIPTION OF THE PRIOR ART

Several prior art patents are noted, which relate particularly to float valves or liquid level controllers for sump pumps and the like. They include the following:

KUO et al. U.S. Pat. No. 5,483,227 issued Jan. 9, 1996;

BARROWS U.S. Pat. No. 5,517,174 issued May 14, 1996;

ORTH et al. U.S. Pat. No. 5,562,423 issued Oct. 8, 1996;

JANESKY U.S. Pat. No. 5,927,955 issued Jul. 29, 1999;

UTKE U.S. Pat. No. 6,069,331 issued May 30, 2000; and

LEE et al. U.S. Pat. No. 6,140,925 issued Oct. 31, 2000.

Several other patents relate more to moisture sensors, including the following:

FISCHER U.S. Pat. No. 3,874,403 issued Apr. 1, 1975 teaches a safety attachment for appliances that may be subject to fluid leakage. Such appliances are, of course, clothes washers or dish washers, in particular. The device includes a fluid sensitive switch which is positioned for exposure to fluid leakage from the appliance—typically, in the region immediately below the appliance. An electrical circuit including a power source interconnects the fluid sensitive switch with a solenoid which supplies water to the appliance. In the event that a leak is detected, the further supply of water to the appliance is precluded.

HATFIELD U.S. Pat. No. 4,020,478 issued Apr. 26, 1977 teaches a device which is specifically intended for mounting into a standard 115 volt conventional outlet. A detachable liquid sensing unit is provided, which includes a cellulose pad that has a pair of electrodes embedded therein, and encased between sheets of perforated plastic film. A connecting conductor with a phone-type jack is also provided, to plug the sensor into the power unit housing. The sensing circuit is provided with an appropriate visual or audio warning indicator, but it relies on being mounted into a conventional electrical outlet, which is its only source of power.

CAPLE U.S. Pat. No. 4,796,658 issued Jan. 10, 1989 teaches an apparatus which is intended to detect basement water which comes particularly as a consequence of a broken water main in the basement. Two sensors are provided, one which extends downwardly into a standard floor drain, and one which sits against the floor. If water in the standard floor drain rises above a predetermined level, the sensor will function to operate a solenoid that will turn off the water flowing in the water supply pipe for the building. Likewise, if moisture is detected on the floor, once again the water supply pipe will be turned off by operation of the solenoid operated switch. Obviously, in order for such an apparatus to work, it requires to be connected to the electrical power supply for the building.

HARDIN U.S. Pat. No. 6,157,307 issued Dec. 5, 2000 teaches a device which will detect and warn of flood water about a building structure. The device is provided with a plurality of selectable remote alarm indicators, and includes a means for detecting the presence of water on the floor, a power circuit with a back up battery capability, a selectable intermittent alarm signal generator, and automatic audio alarm indicators which will indicate either a flood water condition or a low power condition. An appropriate switch is provided to simulate a flood water condition.

SUMMARY OF THE INVENTION

In accordance with one aspect of the present invention, there is provided a self-contained apparatus for detecting the presence of moisture electively at floor level or below floor level, and for issuing an alarm signal when moisture is detected.

The self-contained apparatus of the present invention includes a base portion, a sensor arm, and a mast portion, each of which has first and second ends.

The base portion has an upper surface, and a lower planar surface which is adapted for placement on a floor.

The sensor arm is hingedly connected to the base portion at a respective first end of each, and it has a pair of moisture sensing electrodes located at its second end.

The sensor arm has first and second planar surfaces, and is adapted to underlie the base portion with the first planar surface recessed into a recess which is formed in the lower planar surface of the base portion. The sensor arm is further adapted to extend downwardly from its hinged first end.

When the sensor arm underlies the base portion, the second planar surface of the planar arm is in contact with the floor. When the sensor arm extends downwardly from the base portion, and the lower planar surface of the base portion is in contact with a floor, then the moisture sensing electrodes are located at the predetermined distance below the floor.

The mast portion is also hingedly connected at its first end to the second end of the base portion, and the mast portion is adapted to be upstanding from the base portion when it is in an erected condition.

The mast portion has operating and alarm circuits, an alarm signal output means, and a battery, all located at the second end of the mast portion so as to be elevated from the base portion when the mast portion is in its erected condition.

The pair of moisture sensing electrodes is electrically connected to the operating and alarm circuits.

In general, the distance from the hinged first end of the sensor arm to the moisture sensing electrodes is predetermined, so that when the sensor arm extends downwardly from the base portion and the lower planar surface of the base portion is in contact with a floor, the moisture sensing electrodes are located at the predetermined distance below the floor.

However, the present invention also contemplates that in some instances, the distance from the hinged first end of the sensor arm to the moisture sensing electrodes may be altered.

In keeping with a particular provision of the present invention, when the sensor arm is extended downwardly from the base portion, and the lower planar surface of the base portion is placed on a floor, adhesive means may be interposed between the lower planar surface and the floor.

Another provision of the present invention is that the alarm signal output means may be chosen from the group consisting of audible alarm means, electronic signalling means for transmitting a signal to a remotely located receiver, and combinations thereof.

In a particular embodiment of the present invention, co-operating anchor means are provided at the second end of the base portion and at the first end of the mast portion. They act so as to lock the mast portion in its erected condition when the apparatus is put into place for operation.

The present invention provides that the pair of moisture sensor electrodes may be shaped so as to detect moisture in a region adjacent a floor, when the sensor arm underlies the base portion, and when the apparatus is placed on the floor with the second planar surface of the sensor arm in contact with the floor.

Another embodiment of the present invention has the sole purpose of detecting the presence of moisture in a region below floor level, and issuing an alarm signal when moisture is detected.

Once again, the apparatus includes a base portion, a sensor arm, and a mast portion, each of which has first and second ends.

The base portion has an upper surface, and a lower planar surface which is adapted for placement on a floor. The sensor arm is connected to the base portion at a respective first end of each, and has a pair of moisture sensing electrodes mounted thereon; so that when the apparatus is in place, the moisture sensing electrodes are located at a distance below the floor on which the apparatus rests.

The mast portion is connected at the first end thereof to the second end of the base portion, and is upstanding therefrom.

The mast portion has operating and alarm circuits, an alarm signal output means, and a battery, located at the second end thereof so as to be elevated from the base portion; and the pair of moisture sensing electrodes is electrically connected to the operating and alarm circuits.

This embodiment may also further comprise adhesive means on a lower planar surface of the base portion and adapted to be interposed between the lower planar surface and a floor when the apparatus is in place to detect moisture below floor level.

Also, the mast portion may be hingedly connected at the first end thereof to the second end of the base portion, and is adapted to be upstanding therefrom when in an erected condition. Thus, the operating and alarm circuits, the alarm signal output means, and the battery, are elevated from the base portion when the mast portion is in its erected condition.

This embodiment is otherwise as discussed above.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

The novel features which are believed to be characteristic of the present invention, as to its structure, organization, use and method of operation, together with further objectives and advantages thereof, will be better understood from the following discussion.

The apparatus 10, in keeping with the present invention, is shown in various modes of operation and configurations throughout FIGS. 1 through 6. As discussed, the two principle modes of operation of the present invention, when in its operating configurations, are either to detect the presence of moisture at floor level, or below floor level. These modes of operation are electively selected, and are determined principally by the placement of the sensor arm and its configuration with respect to the remainder of the apparatus.

The three principle structural components of the apparatus, in keeping with the present invention, are a base portion 12, a sensor arm 14, and the mast portion 16. The base portion 12 has a first end 20 and a second end 22. The sensor arm 14 has first end 24 and second end 26; and the mast portion 16 has a first end 28 and a second end 30.

The base portion 12 has an upper surface 34, and a lower planar surface 32 which is adapted for placement on a floor. This is shown particularly at FIGS. 5 and 6, where the base portion 12 is shown sitting on a floor 60.

Figure 1:
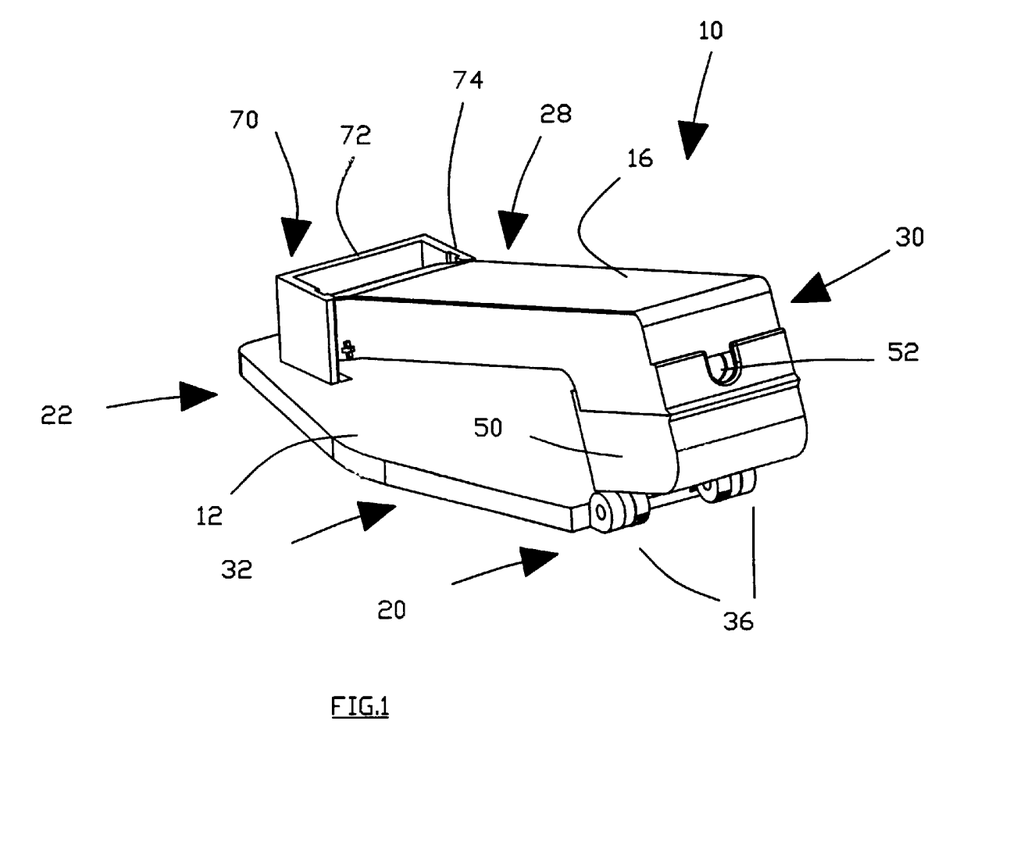
FIG. 1 is a perspective view of an apparatus in keeping with the present invention, in folded condition.
Figure 2:
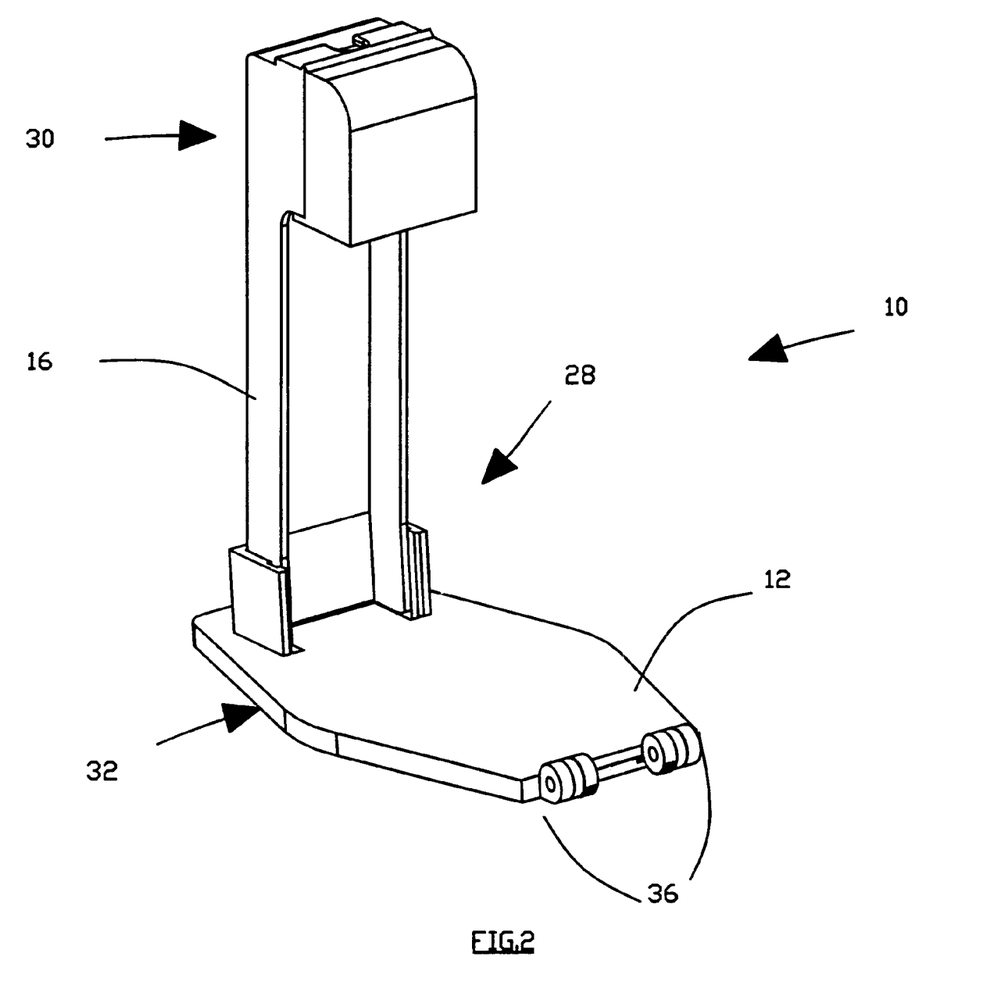
FIG. 2 is a perspective view of the apparatus of the present invention, with the mast in its erected condition.
Figure 3:
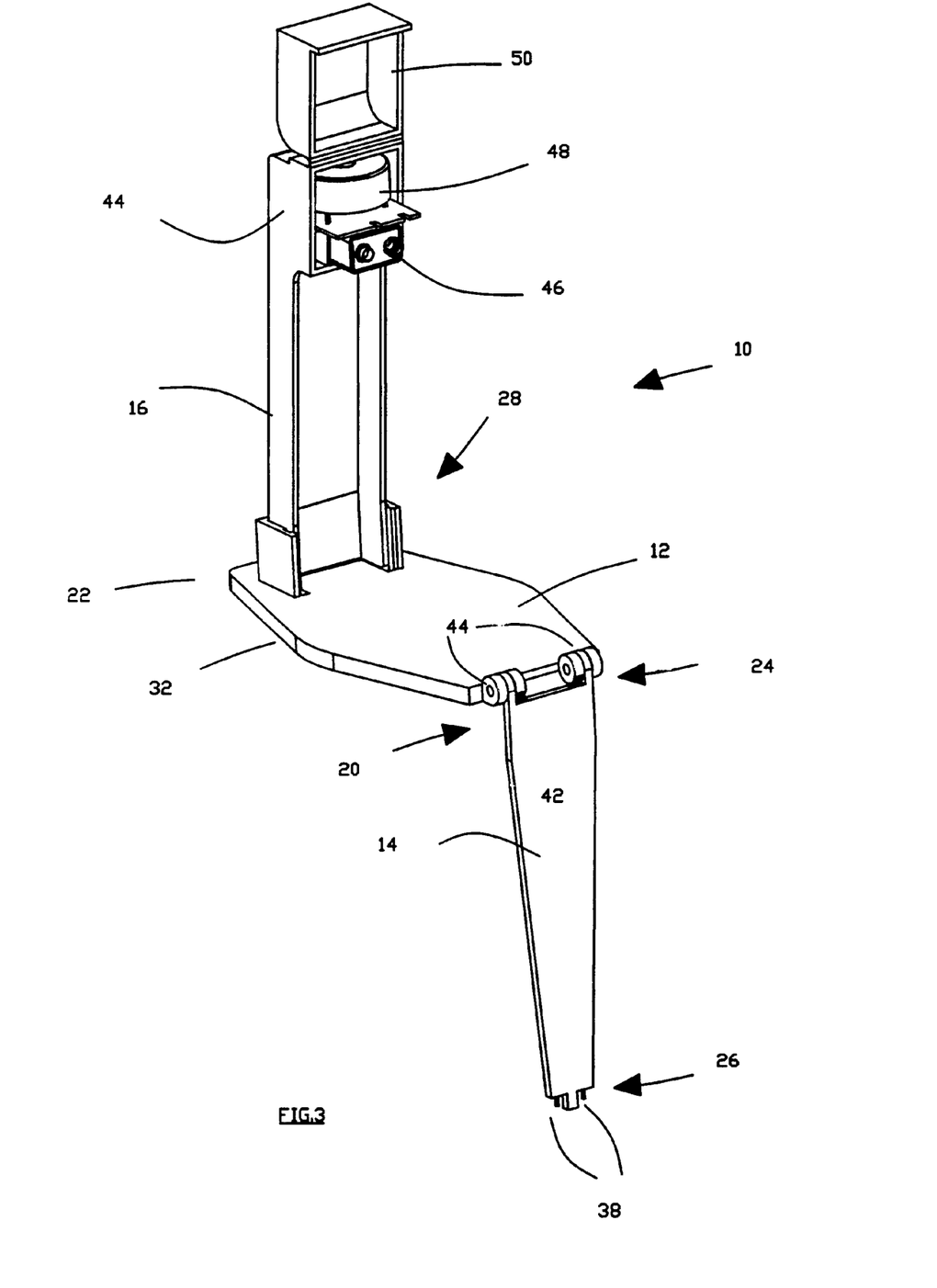
FIG. 3 is a perspective view of the present invention, with the mast in its erected condition, and the circuit compartment at the upper end of the mast being opened, and with the sensor arm extending downwardly.
Figure 4:
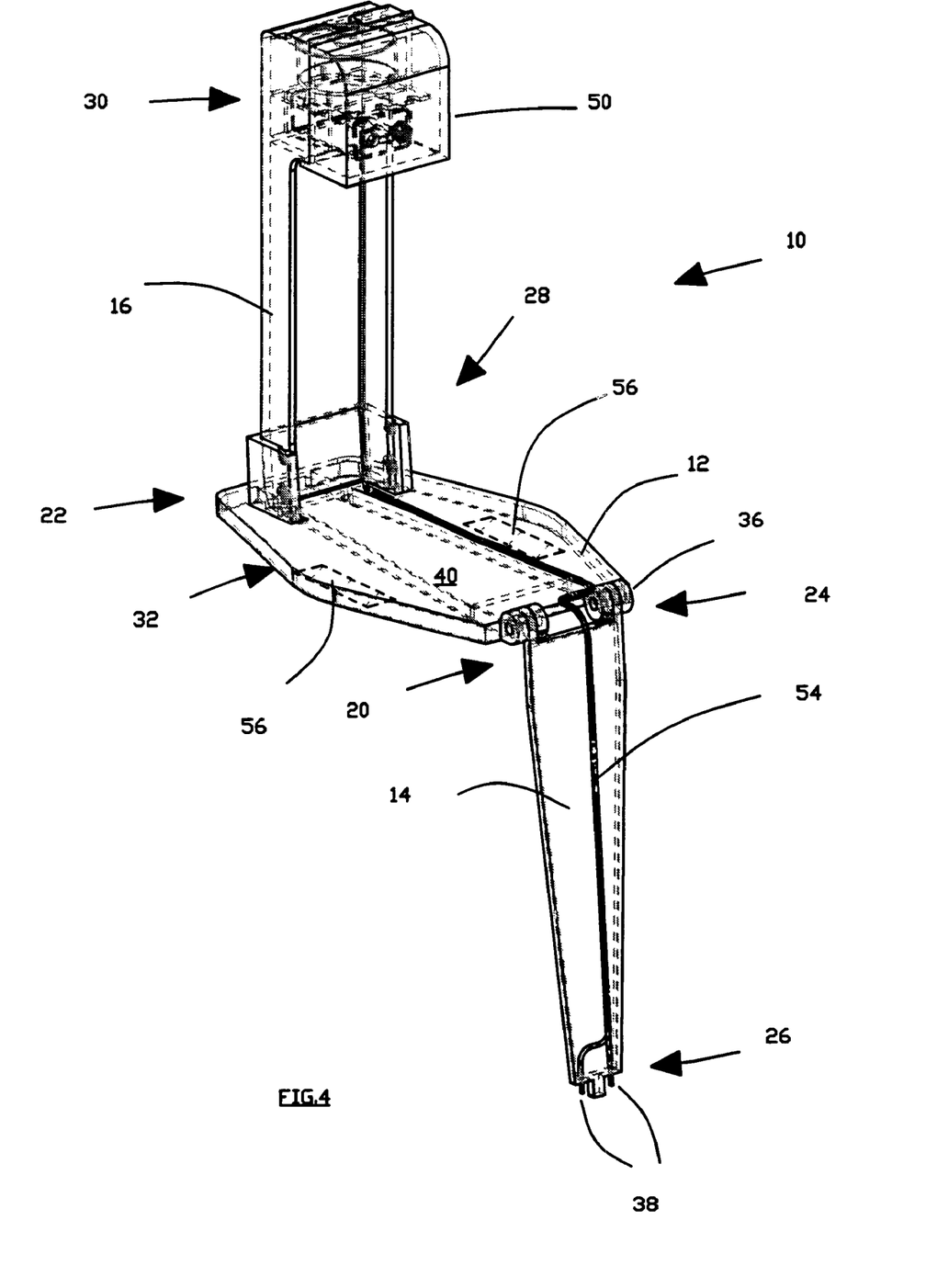
FIG. 4 is a view similar to that of FIG. 3, but showing certain internal details of the apparatus of the present invention.

As can be seen by an examination of FIGS. 1 and 2, with comparison to FIGS. 3 and 4, the sensor arm 14 is hingedly connected by means of a pair of hinges 36, for example, at its first end 24 to the first end 20 of the base portion 12. The sensor arm 14 is fitted with a pair of moisture sensing electrodes 38 which are located at the second end 26 of the sensor arm 14. It should be noted that the precise electrical operating details of apparatus in keeping with the present invention are beyond the scope of the present discussion, and are well known to persons skilled in the art. It is sufficient to note that when a circuit is completed between the pair of moisture sensing electrodes 38 in the presence of water, which is electrically conductive, appropriate notice is taken by the operating and alarm circuits of the apparatus and an appropriate alarm signal is given.

Figure 6:
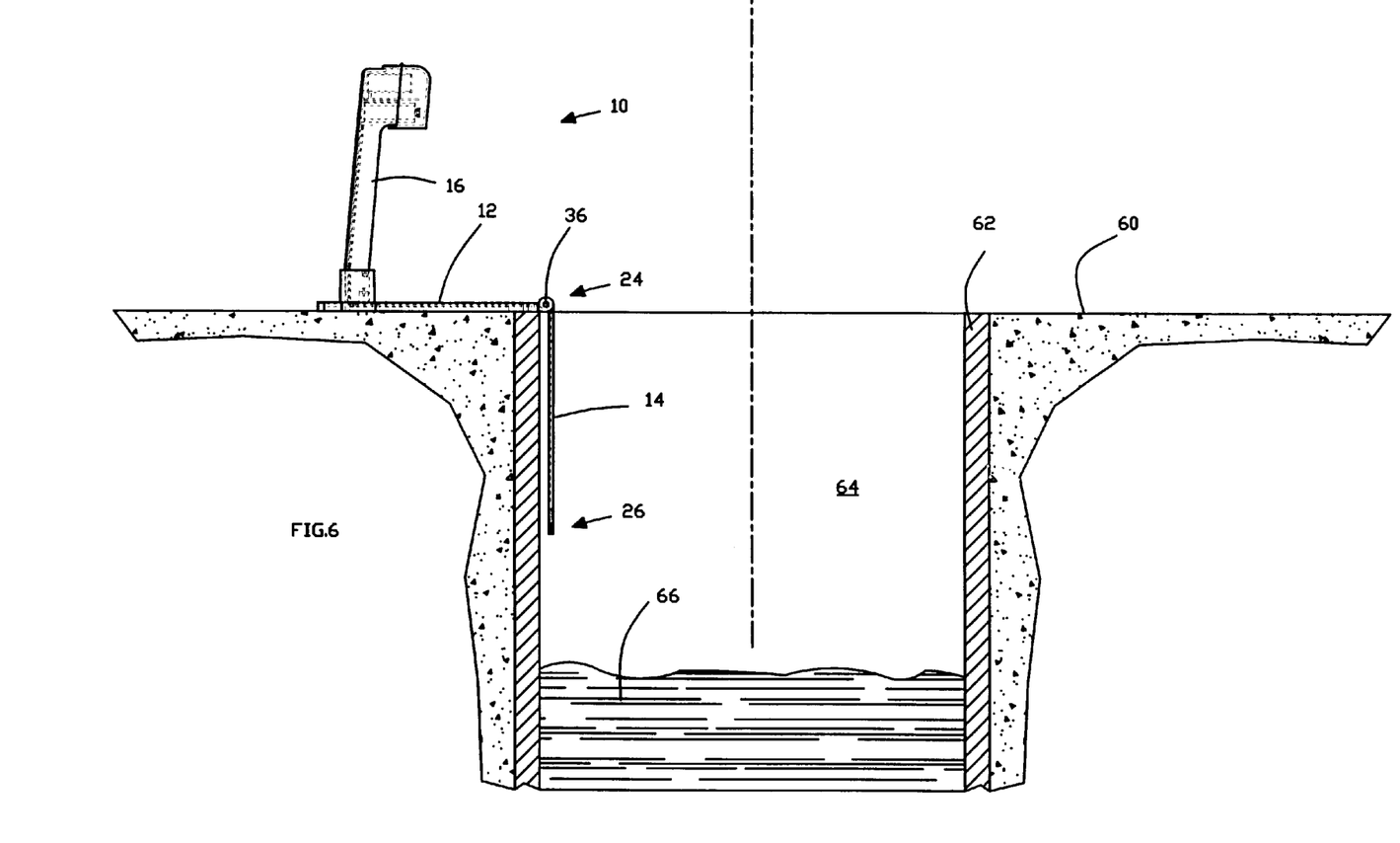
FIG. 6 is a side elevation of a second mode of operation of the present invention, for sensing the rise of water in a sump well beyond a predetermined level.

Inspection of FIGS. 3, 4, and 6, will reveal that the distance from the hinged first end 24 of the sensor arm 14 to the moisture sensing electrodes 38 at the second end 26 of the sensor arm 14, is a fixed or predetermined distance. It follows, therefore, that when the apparatus 10 in keeping with the present invention operates in a water level detecting mode to detect water at a level below the level of the floor, it operates so as to detect that water at a predetermined level which is the length of the sensor arm 14 from the hinges 36 at its first end 24 to the moisture sensing electrodes 38. Typically, that length is in the range of 20 to 25 centimetres.

Figure 5:
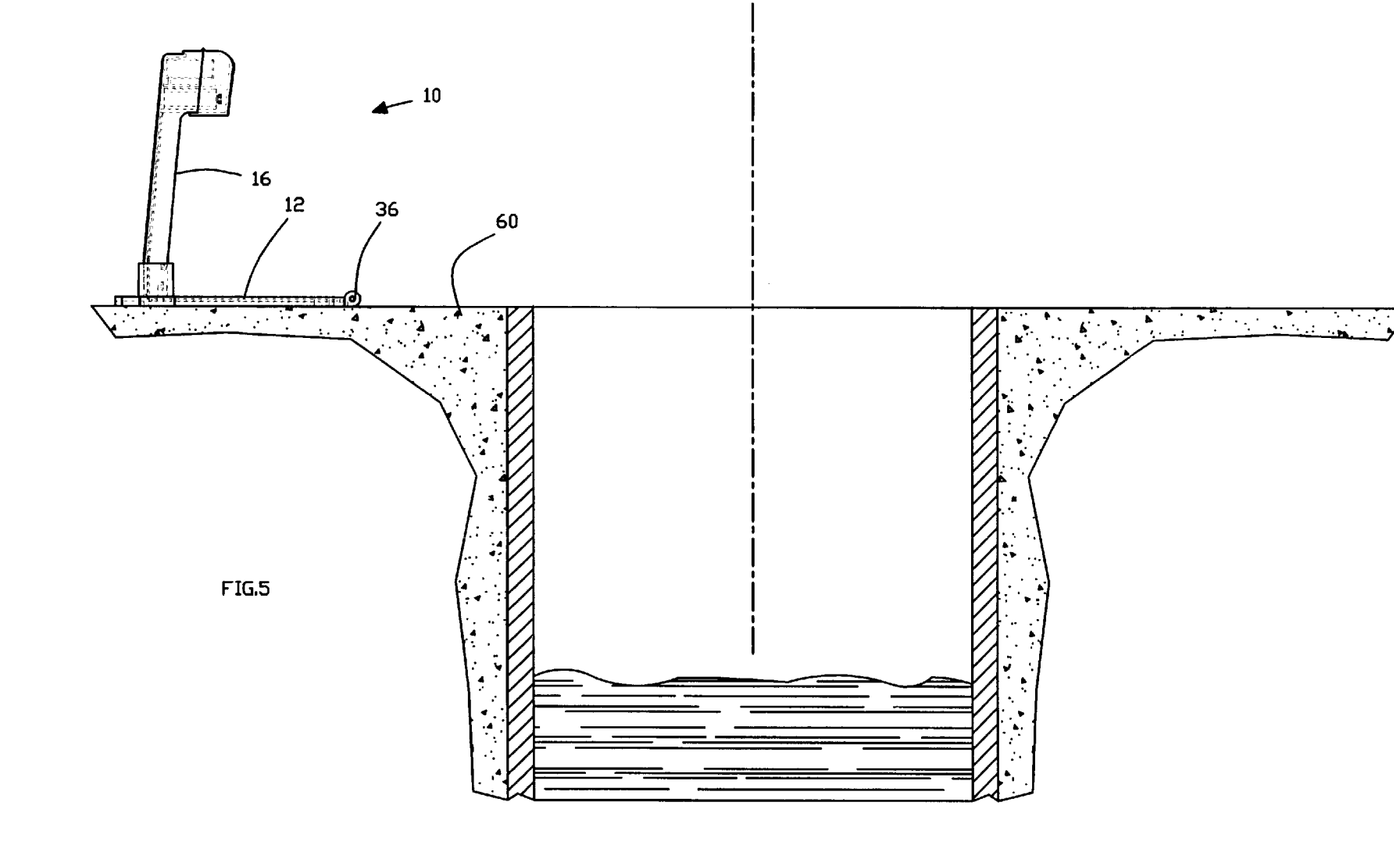
FIG. 5 is a side elevation of apparatus in keeping with the present invention in a first mode of operation, for sensing moisture on the surface of a floor.

Examination of FIGS. 1, 2, and 5 will reveal that the presence of the sensor arm 14 in the apparatus is not evident. That is because the sensor arm 14 is adapted to be received in a recess 40 which is shown in dotted outline in FIG. 4. Recess 40 is formed in the lower planar surface 32 of the base portion 12.

The sensor arm 14 has back and front planar surfaces, or first and second planar surfaces, with the second or front planar surface being indicated at 42 in FIG. 3.

When the apparatus 10 is configured in the manner shown in FIGS. 1, 2, and 5, so that the sensor arm 14 underlies the base portion 12, and is received in its respective recess 40, the second planar surface 42 of the sensor arm 14 is in contact with a floor 60, when placed thereon.

On the other hand, when the sensor arm 14 extends downwardly from the base portion 12, as shown in FIGS. 3, 4, and 6, and the lower planar surface 32 of the base portion 12 is in contact with the floor 60 as shown in FIG. 6, then the moisture sensing electrodes 38 are located at the predetermined distance below the floor, as discussed above.

The mast portion 16 is also hingedly connected at its first end 28 to the second end 22 of the base portion 12. The mast portion 16 is adapted to be upstanding from the base portion 12 when it is in its erected position, as described in greater detail hereafter. The erected condition of the mast portion 16 is shown in all of the figures except FIG. 1.

Operating and alarm circuits are mounted inside a compartment 44 behind battery 46, located at the second end 30 of the mast portion 16. A typical alarm annunciator is shown at 48, and that alarm annunciator might be a bell, horn, buzzer, or other device which creates an audible sound.

Typically, the compartment 44 is closed by a cover 50. When the cover 50 is closed, an opening 52 at the top of the mast portion 16 is formed so as to permit an audible alarm to be heard more clearly from the alarm annunciator 48.

It will be evident from an examination of the drawings that when the mast portion 16 is in its erected condition, the compartment 44 and the operating and alarm circuits, and the alarm signal output means and battery contained therein, are elevated above the base portion 12—and, therefore, are elevated above the floor when the apparatus is placed on a floor 60. The typical elevation of the compartment 44 above the floor level is in the range of 20 to 25 centimetres.

Obviously, the pair of moisture sensing electrodes is electrically connected by way of appropriate cabling 54 to the operating and alarm circuits in the compartment 44.

When the sensor arm 14 is extended downwardly from the base portion 12, as shown in FIGS. 3, 4, and 6, and the lower planar surface 32 of the base portion 12 is in contact with a floor 60, there may be adhesive means 56 (see FIG. 4) interposed between the lower planar surface 32 of the base portion 12 and the floor 60. Such adhesive means are typically double-sided adhesive tape, although means such as hook and loop fasteners may be appropriate in some circumstances.

Turning briefly to FIGS. 5 and 6, the two principal modes of operation of the apparatus 10 in keeping with the present invention are shown. In FIG. 5, the mast 16 is shown in its erected condition, and the base portion 12 together with the sensor arm 14 are shown in folded together condition with the sensor arm 14 being received in its recess 40. Obviously, the apparatus 10 could be placed on any floor, anywhere, because its purpose in the mode shown in FIG. 5, in that configuration, is to sense the presence of moisture on the floor 60.

FIG. 6, on the other hand, shows the second principal mode of operation of the apparatus 10, where it is placed on the floor 60 and overhangs a wall 62 of a sump well 64, so as to extend downwardly thereinto. Obviously, as the level of the water 66 advances upwardly in the well 64 and reaches the level of the second end 26 of the sensor arm 14, and the moisture sensing electrodes 38 installed therein, an alarm will be given.

As indicated above, the nature of the alarm is generally an audible alarm. However, the annunciator 48 may be replaced by, or joined by, a signalling means which will generate a very low power signal which may be transmitted to a remotely located receiver. Such signalling devices are well known and are beyond the scope of the present invention. Typically, signalling devices of the sort spoken of immediately above will send a useful signal a short distance of, say, 30 to 60 metres.

The apparatus 10 of the present invention may conveniently be provided with a cooperating anchor for the mast portion 16, as shown generally at 70. That anchor conveniently comprises a channel 72, having a pair of grooves 74 formed in the inside edges thereof as seen in FIG. 1. Anchor pins 76 fit into the grooves 74 when the mast portion 16 is elevated into its erected position, and it is thereby locked into place.

When the apparatus 10 of the present invention is in its floor moisture detecting mode and configuration, as shown in FIGS. 2 and 5, the function of the moisture sensing electrodes 38 is to sense or detect moisture in a region which is adjacent the floor. Accordingly, the moisture sensing electrodes 38 may be appropriately shaped so as to sense the presence of moisture at a depth of, for example, no more than one or two millimetres.

The configuration shown in FIG. 1 is not generally considered to be an operating configuration because one purpose of the present invention is to elevate the electronic circuitry above the floor when the mast portion 16 is in its erected position. However, the configuration shown in FIG. 1 is that which is convenient for storage of the apparatus 10, such as when the apparatus is on the shelf, waiting for sale, or in transit, or having been set aside in dry weather conditions when flooding or moisture seepage is unlikely.

There has been described an apparatus whose purpose is to detect the presence of moisture electively at floor level or below floor level, depending on its configuration. The apparatus is self-contained, so that it operates quite independently of any requirement for conventional 115 volt AC power. Obviously, self-testing circuits, low battery power and voltage circuits, and the like, may be included as necessary and appropriate, and such matters are beyond the scope of the present invention but are well known to those skilled in the art.

In another embodiment of the present invention, the apparatus may be employed strictly for purposes of detecting water level above a predetermined level in a sump well. The apparatus is essentially identical to that which has been illustrated and discussed, except to note that the sensor arm 14 need not be hingedly attached to the base portion 12.

Rather, the sensor arm 14 can be fixed in place with respect to the base portion 12.

Moreover, the moisture sensing electrodes 38 may be mounted on the sensor arm 14 in any embodiment of the present invention in a manner such that, when the sensor arm is in the configuration shown particularly in FIGS. 3 through 6, the placement of the moisture sensing electrodes may be altered so that adjustments may be made as to the water level before the floor level at which an alarm will be given.

Also, it may be possible when the sensing electrodes 38 are, indeed, in a fixed position at the end of the sensor arm 14, to angle the sensor arm 14 away from the wall of the sump well, thereby raising the level at which an alarm will be given.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

What is claimed is:

1. A self-contained apparatus for detecting the presence of moisture effectively at floor level or below floor level, and for issuing an alarm signal when moisture is detected, comprising:
    a base portion, a sensor arm, and a mast portion;
    wherein each of said base portion, said sensor arm, and said mast portion, has a first end and a second end;
    wherein said base portion has an upper surface, and a lower planar surface which is adapted for placement on a floor;
    wherein said sensor arm is hingedly connected to said base portion at a respective first end of each, and has a pair of moisture sensing electrodes located at its second end;
    wherein said sensor arm has first and second planar surfaces, and is adapted to underlie said base portion with said first planar surface recessed into a recess formed in said lower planar surface of said base portion, and wherein said sensor arm is further adapted to extend downwardly from said hinged first end;
    wherein, when said sensor arm underlies said base portion, said second planar surface of said sensor arm is in contact with a floor; and when said sensor arm extends downwardly from said base portion, and said lower planar surface of said base portion is in contact with a floor, said moisture sensing electrodes are located at a distance below the floor;
    wherein said mast portion is hingedly connected at said first end thereof to said second end of said base portion, and is adapted to be upstanding therefrom when in an erected condition;
    wherein said mast portion has operating and alarm circuits, an alarm signal output means, and a battery, located at the second end thereof so as to be elevated from said base portion when said mast portion is in its erected condition; and
    wherein said pair of moisture sensing electrodes is electrically connected to said operating and alarm circuits.

2. The apparatus of claim 1, wherein the distance from said hinged first end of said sensor arm to said moisture sensing electrodes is predetermined, so that when said sensor arm extends downwardly from said base portion and said lower planar surface of said base portion is in contact with a floor, said moisture sensing electrodes are located at said predetermined distance below the floor.

3. The apparatus of claim 1, wherein the distance from said hinged first end of said sensor arm to said moisture sensing electrodes may be altered.

4. The apparatus of claim 1, wherein, when said sensor arm is extended downwardly from said base portion and said lower planar surface of said base portion is placed on a floor, adhesive means are interposed between said lower planar surface and the floor.

5. The apparatus of claim 1, wherein said alarm signal output means is chosen from the group consisting of audible alarm means, electronic signalling means for transmitting a signal to a remotely located receiver, and combinations thereof.

6. The apparatus of claim 1, further comprising co-operating anchor means at said second end of said base portion and said first end of said mast portion, so as to lock said mast portion in its erected condition when said apparatus is put into place for operation.

7. The apparatus of claim 1, wherein said pair of moisture sensing electrodes is shaped so as to detect moisture in a region adjacent a floor when said sensor arm underlies said base portion, and said apparatus is placed on a floor with said second planar surface of said sensor arm in contact therewith.

8. A self-contained apparatus for detecting the presence of moisture in a region below floor level, and for issuing an alarm signal when moisture is detected, comprising:
    a base portion, a sensor arm, and a mast portion;
    wherein each of said base portion, said sensor arm, and said mast portion, has a first and second end;
    wherein said base portion has an upper surface, and a lower planar surface which is adapted for placement on a floor;
    wherein said sensor arm is connected to said base portion at a respective first end of each, and has a pair of moisture sensing electrodes mounted thereon, so that when said apparatus is in place said moisture sensing electrodes are located at a distance below the floor on which said apparatus rests;
    wherein said mast portion is connected at said first end thereof to said second end of said base portion, and is upstanding therefrom;
    wherein said mast portion has operating and alarm circuits, an alarm signal output means, and a battery, located at the second end thereof so as to be elevated from said base portion; and
    wherein said pair of moisture sensing electrodes is electrically connected to said operating and alarm circuits.

9. The apparatus of claim 8, wherein the distance from said first end of said sensor arm to said moisture sensing electrodes may be altered.

10. The apparatus of claim 8, further comprising adhesive means on a lower planar surface of said base portion and adapted to be interposed between said lower planar surface and a floor when said apparatus is in place to detect moisture below floor level.

11. The apparatus of claim 8, wherein said mast portion is hingedly connected at said first end thereof to said second end of said base portion, and is adapted to be upstanding wherefrom when in an erected condition;
    whereby said operating and alarm circuits, said alarm signal output means, and said battery, are elevated from said base portion when said mast portion is in its erected condition.

12. The apparatus of claim 8, wherein said alarm signal output means is chosen from the group consisting of audible alarm means, electronic signalling means for transmitting a signal to a remotely located receiver, and combinations thereof.

13. The apparatus of claim 11, further comprising co-operating anchor means at said second end of said base portion and said first end of said mast portion, so as to lock said mast portion in its erected condition when said apparatus is put into place for operation.

* * * * *